United States Patent [19]

Burness et al.

[11] 4,171,976

[45] Oct. 23, 1979

[54] HOMOPOLYMERIZATION INHIBITION OF PHOTOGRAPHIC HARDENERS

[75] Inventors: Donald M. Burness, Rochester; Charles J. Wright, Webster, both of N.Y.

[73] Assignee: Eastman Kodak Company, Rochester, N.Y.

[21] Appl. No.: 885,227

[22] Filed: Mar. 10, 1978

[51] Int. Cl.$^2$ .................... G03C 1/30; C09K 15/16; C09H 7/00

[52] U.S. Cl. .................... 96/111; 96/88; 260/112 R; 260/117; 106/125; 252/182; 252/402; 252/405

[58] Field of Search .................... 96/111, 88, 50 PT; 260/112, 117, 607 AL; 106/125; 252/182, 402, 405

[56] References Cited

U.S. PATENT DOCUMENTS

| | | | |
|---|---|---|---|
| Re. 29,305 | 7/1977 | Burness et al. | 96/111 |
| 2,415,624 | 2/1947 | Brown et al. | 96/84 R |
| 3,551,507 | 12/1970 | Sakuragi et al. | 252/405 |
| 3,556,794 | 1/1971 | Margerum | 96/115 P |
| 3,640,720 | 2/1972 | Cohen | 96/111 |
| 3,832,179 | 8/1974 | Edens | 96/56 |
| 4,039,520 | 8/1977 | Habu et al. | 96/111 |

FOREIGN PATENT DOCUMENTS

1399450 7/1975 United Kingdom .................... 96/109

OTHER PUBLICATIONS

Ulbricht, J.: "Inhibitors and Inhibition Constants in Free Radical Polymerization," Polymer Handbook, 1966, pp. II-71-75; p. 2, line 37 thru p. 3, line 3.

Bartlett et al.: "Dilatomic Studies of the Behavior of Some Inhibitors and Retarders in the Polymerization of Liquid Vinyl Acetate," JACS, vol. 72, 1950, pp. 1050-1059; p. 2, lines 30 thru 36.

T. H. James, *The Theory of the Photographic Process,* 4th Ed., MacMillan, 1977, pp. 77-87; p. 1, lines 31 through 36.

Frank & Adams, "The Relative Efficiency of Some Polymerization Inhibitors", *JACS,* vol. 68, 1946, p. 908, p. 2, lines 24 thru 30.

*Primary Examiner*—Won H. Louie, Jr.
*Attorney, Agent, or Firm*—Carl O. Thomas

[57] ABSTRACT

It is disclosed to inhibit homopolymerization of a bis(-vinylsulfonyl)alkane hardener for a hydrophilic colloid useful in forming a layer of a photographic element by associating with the hardener a nitro-substituted aromatic compound.

19 Claims, No Drawings

HOMOPOLYMERIZATION INHIBITION OF PHOTOGRAPHIC HARDENERS

BACKGROUND OF THE INVENTION

1. Field of the Invention

This invention relates to the homopolymerization inhibition of bis(vinylsulfonyl)alkane hardeners. In one aspect, the invention relates to compositions comprising a hydrophilic colloid, a bis(vinylsulfonyl)alkane hardener and an inhibitor for homopolymerization of the hardener. In another aspect, the invention relates to methods for inhibiting homopolymerization of bis(vinylsulfonyl)alkane hardeners in preparing photographic elements. In still another aspect, the invention relates to photographic elements hardened with a composition comprising a homopolymerization inhibited bis(vinylsulfonyl)alkane hardener.

2. Description of the State of the Art

In the photographic arts hydrophilic colloids, typically refined gelatin, have been used in photographic elements to form layers, such as radiation-sensitive layers (e.g., silver halide emulsion layers), interlayers, subbing layers and overcoat layers. Various addenda are conventionally incorporated in the layers, including addenda to alter the properties of the hydrophilic colloids present. It has been recognized previously in the art that without special modifiers hydrophilic colloids such as gelatin are easily abraded and ingest large quantities of water when brought into contact with aqueous solutions, thereby causing an undesirable amount of swelling. Also, unmodified colloid coatings tend to melt at relatively low temperatures, thereby limiting their temperature range of utility. To obviate these deficiencies certain addenda generically designated as "hardeners" are incorporated into hydrophilic colloids intended to be used in forming photographic element layers. Both inorganic and organic hardeners are known. A summary of hardeners is presented by T. H. James, *The Theory of the Photographic Process*, 4th Ed., MacMillan, 1977, pp. 77–87. The terms "forehardened" and "forehardener" are employed when the hardener is associated with hydrophilic colloid in the course of manufacturing a photographic element. The terms "prehardened" and "prehardener" are employed when the hardener is associated with a hydrophilic colloid layer of a photographic element in a processing solution preceding the developer bath for the element.

Among hardeners of the active olefin type, a preferred class of hardeners particularly useful as forehardeners are bis(vinylsulfonyl)alkane hardeners. Bis(vinylsulfonyl)alkane hardeners are believed to be effective as hardeners as a result of their ability to crosslink polymers making up the colloid. One disadvantage that has been observed in using bis(vinylsulfonyl)alkane hardeners is that these hardeners, particularly the more active ones, will homopolymerize. Homopolymerization can occur before the hardeners are associated with the hydrophilic colloid and it can occur as a competing reaction after association. The tendency of the hardeners to homopolymerize is disadvantageous in requiring careful selection of hardener preparation and handling conditions and in causing hardener to become unavailable for the desired crosslinking reaction with the hydrophilic colloid.

Polymerization inhibitors are known in the art. Frank and Adams, "The Relative Efficiency of Some Polymerization Inhibitors", *Journal of the American Chemical Society* (JACS), Vol. 68, 1946, p. 908, lists a number of polymerization inhibitors, including picric acid and trinitrobenzene, and reports their effects on styrene, 3,4-dichlorostyrene and 5-ethyl-2-vinylpyridine. Bartlett and Kwart, "Dilatomic Studies of the Behavior of Some Inhibitors and Retarders in the Polymerization of Liquid Vinyl Acetate", *JACS*, Vol. 72, 1950, pp. 1050–1059, discusses the polymerization inhibiting effectiveness of p-nitrotoluene, nitrobenzene, dinitrodurene and dinitrobenzene on inhibiting polymerization of vinyl acetate. J. Ulbricht, "Inhibitors and Inhibition Constants in Free Radical Polymerization", *Polymer Handbook*, 1966, pp. II-71–75, reports quantitatively inhibiting effects of a number of nitrobenzene and nitrobenzoic acid compounds on monomers, such as methyl acrylate, methyl methacrylate, vinyl acetate and styrene. The gross variations in the numbers reported by Ulbricht effectively refute the statement by Frank and Adams that a good inhibitor for one monomer is likely to be a good inhibitor for another. Margerum U.S. Pat. No. 3,556,794, issued Jan. 19, 1971, discloses in column 7, lines 20 through 60, for example, ultraviolet responsive desensitizers for photopolymers of the type described, for example, in column 9, lines 13 through 22. A variety of nitro-substituted benzoic acid and ester desensitizers are disclosed and a variety of vinyl monomers.

The use of nitro-substituted aromatic compounds, such as nitrobenzenes, nitrobenzoic acid, and the like, in photographic elements is known in the art. Pollett et al U.K. Pat. Nos. 1,399,449 and 1,399,450, disclose the use of nitro-substituted aromatic compounds to stabilize silver halide photographic elements against fog formation during high temperature processing (greater than 30° C.). Edens U.S. Pat. No. 3,832,179, issued Aug. 27, 1974, discloses the use of nitrobenzoic acids to suppress fog formation in color photographic elements. Brown et al U.S. Pat. No. 2,415,624, issued Feb. 11, 1947, discloses incorporating dinitrobenzoic acid in an overcoat of a photographic element to act as a filter for ultraviolet light. None of these patents disclose the use of hardeners of the vinylsulfonyl type.

Since inhibition of homopolymerization of bis-(vinylsulfonyl)alkane hardeners must be achieved while not interfering with the ability of these hardeners to crosslink with the hydrophilic colloid, it is not surprising that among compounds investigated prior to this invention as homopolymerization inhibitors for photographic bis(vinylsulfonyl)alkane hardeners only hydroquinone has been identified as useful. Burness et al U.S. Pat. No. 3,841,872, issued Oct. 15, 1974, and corresponding U.S. Pat. No. Re. 29,305, reissued July 12, 1977, disclose examples wherein hydroquinone is employed in the preparation of bis(vinylsulfonyl)alkane hardeners. In addition to being limited in the homopolymerization inhibition effect obtained, particularly with the more active hardeners, hydroquinone also exhibits certain other disadvantageous properties, such as (1) formation of colored impurities and (2) formation of addition products which are inactive or insoluble.

STATEMENT OF THE INVENTION

In accordance with the invention, it has been found that bis(vinylsulfonyl)alkane hardeners can be inhibited against homopolymerization without interfering with their utility as hardeners—i.e., hydrophilic colloid crosslinking agents—by combining with the hardener a homopolymerization inhibiting amount of a nitro-substituted aromatic compound.

In one embodiment this invention is directed to a photographic hardener composition comprising a bis-(vinylsulfonyl)alkane hardener and an amount sufficient to inhibit homopolymerization of the hardener of a nitro-substituted aromatic compound.

In another embodiment this invention is directed to an aqueous coating composition useful as a layer of a photographic element comprising a hydrophilic colloid at least partially forehardened with a bis(vinylsulfonyl)alkane hardener. The composition comprises an essentially nonvolatile nitro-substituted aromatic compound present in an amount sufficient to inhibit homopolymerization of the hardener.

In still another embodiment this invention is directed to a process of hardening an aqueous coating composition useful as a layer of a photographic element comprising adding a bis(vinylsulfonyl)alkane hardener to a hydrophilic colloid. The improvement comprises inhibiting homopolymerization of the hardener with an essentially nonvolatile nitro-substituted aromatic compound.

In yet another embodiment this invention is directed to a process of hardening a hydrophilic colloid-containing layer of a photographic element by adding a bis(vinylsulfonyl)alkane hardener to a coating composition containing the hydrophilic colloid and coating the composition onto a photographic support. The improvement comprises inhibiting homopolymerization of the hardener with an essentially nonvolatile nitro-substituted aromatic compound.

In an additional embodiment this invention is directed to a photographic element comprising a support and, coated on the support, one or more layers, at least one of which is radiation-sensitive, containing a hydrophilic colloid at least partially forehardened with a bis-(vinylsulfonyl)alkane hardener. The improvement comprises an essentially nonvolatile nitro-substituted aromatic compound present with the hardener in an amount sufficient to inhibit homopolymerization of the hardener.

In the foregoing embodiments the nitro-substituted aromatic compound can be of the formula:

$$(NO_2)_n\text{—Ar—}(Ball)_{m-1}$$

where
Ar is an aromatic hydrocarbon of from 6 to 12 carbon atoms;
Ball is a polar group; and
n and m are independently chosen from among integers of the value 1, 2 and 3, provided that when Ar is a benzene moiety m is at least 2 and the sum of m+n is 5 or less.

DESCRIPTION OF THE PREFERRED EMBODIMENTS

As indicated above, one embodiment of the invention is a composition comprising a bis(vinylsulfonyl)alkane hardener and a homopolymerization inhibiting amount of an essentially nonvolatile nitro-substituted aromatic compound.

Any conventional bis(vinylsulfonyl)alkane photographic hardener can be used in the practice of this invention. Such hardeners are illustrated by those disclosed in Burness et al U.S. Pat. No. 3,841,872 and its reissue U.S. Pat. No. Re. 29,305, cited above, and here incorporated by reference. Although not specifically investigated, it is believed that bis(vinylsulfonyl)alkene and bis(vinylsulfonylalkyl)benzene hardeners, also disclosed by the above-cited Burness et al patents, should also be useful in the practice of this invention.

The homopolymerization inhibitors employed in the practice of this invention are surprisingly most effective with the most highly active bis(vinylsulfonyl)alkane hardeners. Because of their activity as well as their response to homopolymerization inhibition, the preferred bis(vinylsulfonyl)alkane hardeners employed in the practice of this invention are those represented by the following formula:

$$CH_2=CHSO_2-(CH_2)_r-SO_2CH=CH_2 \quad (I)$$

where
r is selected from among the integers 1, 2 and 3.

Specific preferred bis(vinylsulfonyl)alkane hardeners are bis(vinylsulfonyl)methane, bis(vinylsulfonyl)ethane and bis(vinylsulfonyl)propane. The tendency of the hardeners toward homopolymerization in the absence of an inhibitor is directly related to their hardening activity.

The nitro-substituted aromatic compounds employed as homopolymerization inhibitors are characterized by at least one nitro substituent bonded in a resonant relationship to an aromatic ring, as in the case of a nitro-substituted benzene ring. Where the hardener is being stored, for example, between synthesis and use in photographic coating, both relatively volatile and essentially nonvolatile nitro-substituted aromatic compounds can be employed as homopolymerization inhibitors with almost equal advantage, since the temperature of hardener storage can be readily controlled to avoid any substantial evaporative loss of the inhibitor. On the other hand, to achieve homopolymerization inhibition under actual hardening conditions, essentially nonvolatile nitro-substituted aromatic compounds are preferred. Since hardening of hydrophilic colloids is a comparatively slow reaction, even with the most active hardeners, typically measured in days or weeks, the homopolymerization inhibitor is preferably sufficiently nonvolatile to remain in the composition containing the hardener for at least the period of time required for substantial completion of forehardening. Essentially nonvolatile nitro-subsitituted aromatic compounds are particularly advantageous in the manufacture of photographic elements, since it is conventional practice to blend the hardener and the hydrophilic colloid to be hardened just prior to coating onto a photographic support and immediately thereafter to dry the coating at elevated temperatures approaching 100° C. To be considered substantially nonvolatile and therefore preferred for homopolymerization inhibition in photographic coating applications, at least half (preferably at least 90 percent, most preferably substantially all) of the nitro-substituted aromatic compound should be capable of remaining associated with the hardener until hardening is substantially completed.

To achieve the preferred essentially nonvolatile characteristics the aromatic homopolymerization inhibitors typically include two separate or fused benzene rings, ballasting substituents in addition to the nitro substituents or a combination of both. Ballasting substituents for the purpose of reducing organic addenda volatility and mobility are well known to those skilled in photographic chemistry. The preferred ballasting groups for incorporation in the homopolymerization inhibitors are those which reduce the volatility of the compounds while enhancing (or at least retaining) the water solubility of the compounds in the contemplated concentrations of use. By proper selection of ballasting groups other properties of the compounds, such as human tolerance levels and odor, can be favorably influenced. For example, dinitrobenzoic acids can be tolerated in significantly higher concentration levels than dinitrobenzenes. Combining lowered volatility with higher tolerance levels results in very significantly improved inhibitors from a manufacturing viewpoint.

The preferred nitro-substituted aromatic homopolymerization inhibitors employed in the practice of this invention are those represented by the following formula:

$$(NO_2)_n—Ar—(Ball)_{m-1} \tag{II}$$

where
- Ar is an aromatic hydrocarbon of from 6 to 12 carbon atoms, such as a benzene, biphenyl or naphthalene moiety;
- Ball is a polar group (e.g., a hydroxy, a formyl, an acyl, a carboxyl, a sulfo, an ester, a carbamoyl, a hydroxyalkylamino, an alkoxy, an alkylthio or similar group); and
- n and m are independently chosen from among integers 1, 2 and 3, provided that when Ar is a benzene moiety m is at least 2 and the sum of m+n is 5 or less.

In a specifically preferred form the nitro-substituted homopolymerization inhibitors employed in the practice of this invention are those represented by the following formula:

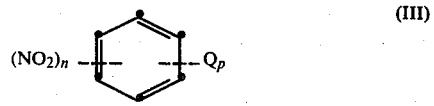

(III)

where
- Q is COZ or SO₂Z;
- Z is —OM, —OR or —NR₂;
- R is hydrogen or alkyl of from 1 to 6 carbon atoms, most preferably an alkyl group of from 1 to 3 carbon atoms;
- M is a salt-forming cationic moiety, such as an alkali metal or a cationic group containing a quaternized nitrogen atom;
- n is an integer of the value 1, 2 or 3; and
- p is an integer of the value 1 or 2, the sum of n+p being 4 or less.

Exemplary of specific nitro-substituted aromatic homopolymerization inhibitors useful in the practice of this invention are the following:
picric acid
2,4-dinitrobenzoic acid
3,4-dinitrobenzoic acid
2,5-dinitrobenzoic acid
3,5-dinitrobenzoic acid
o-nitrobenzoic acid
m-nitrobenzoic acid
p-nitrobenzoic acid
2,4,6-trinitrobenzoic acid
2,4-dinitrobenzenesulfonic acid
N,N-bis(2-hydroxyethyl)-3,5-dinitrobenzamide
4,4'-dinitrobiphenyl
4,4'-dinitrobiphenyl-2,2'-dicarboxylic acid
2-(4-nitrobenzyl)benzoic acid
4-(4-nitrobenzyl)benzoic acid
4-nitrophenylacetic acid
4-nitrophthalic acid
1,2,3-trinitro-4,5-dimethoxybenzene
p-nitrobenzamide
3-nitroacetophenone
4-pentadecyl-1,3-dinitrobenzene
4-n-hexadecylthio-1,3-dinitrobenzene
4-n-hexadecyloxy-1,3-dinitrobenzene The above compounds, although in the form of the free acid, could also be present in the form of a salt-e.g., the sodium or potassium salt—or an ester-e.g., a methyl, ethyl or propyl ester. Although carboxylic acid substituents are predominantly designated, a sulfonic acid substituent could be substituted therefor in each instance.

To be effective in inhibiting homopolymerization of the bis(vinylsulfonyl)alkane hardener the nitro-substituted aromatic compound is associated with the hardener while all or a portion of the hardener remains in its unreacted monomeric form. It is generally preferred that homopolymerization inhibitor be in the same hydrophilic colloid-containing composition as the hardener when it is coated onto a photographic support. The hardener and the inhibitor can be brought together in any convenient way. For example, the inhibitor can be blended with the hydrophilic colloid to be hardened so that upon addition of the hardener the inhibitor is already present. It is generally preferred that the inhibitor be blended with the hardener before the hardener is blended with the hydrophilic colloid. It is conventional practice to form bis(vinylsulfonyl)alkane hardeners by the dehydrohalogenation of the corresponding 2-haloethylsulfonyl hardener precursors. By placing the inhibitor in the solution containing the hardener precursor and then performing the dehydrohalogenation reaction the inhibitor is associated with the bis(vinylsulfonyl)alkane hardener from its inception, and no opportunity is afforded for homopolymerization to occur before the inhibitor can be introduced. In a preferred specific illustrative form, a 2-chloroethylsulfonyl hardener precursor, such as bis(2-chloroethylsulfonyl)methane, is dissolved in an organic solvent, such as acetone, along with the inhibitor, and dehydrohalogenation is performed by adding one mole of a lower alkylamine, such as triethylamine, for each equivalent of the 2-chloroethylsulfonyl hardener precursor. The acetone can be removed, such as by evaporation, to leave the bis(vinylsulfonyl)alkane hardener and inhibitor as a solid residue. The solid residue can be stored for any convenient length of time before use in hardening a hydrophilic colloid. Addition of the hardener to the hydrophilic colloid in the presence of the inhibitor is identical to the procedures conventionally employed in the absence of the inhibitor.

Any hydrophilic colloid known to be hardenable by a vinylsulfonyl hardener can be employed in the practice of this invention. The hydrophilic colloids which are useful with the above vinylsulfonyl hardeners can be formed from one or more hydrophilic, water-permeable, colloid-forming, natural or synthetic polymers. Specific polymers which can be hardened include hardenable polymers such as gelatin and hardenable gelatin derivatives, colloidal albumin, acid- or water-soluble vinyl polymers, cellulose derivatives, proteins, various polyacrylamides, dispersed polymerized vinyl compounds, particularly those which increase the dimensional stability of photographic materials as exemplified by amine-containing polymers of alkyl acrylates, methacrylates, acrylic acid, sulfoalkyl acrylates and methacylates, acrylic acid-acrylate copolymers, and the like. Hardenable gelatin derivatives include those illustrated by Yamamoto et al U.S. Pat. No. 3,923,517, particularly gelatin derivatives produced by reacting carboxylic acid anhydrides or halides with gelatin (e.g., acetylated gelatin, phthalated gelatin and the like) as further illustrated by Barnes et al U.S. Pat. No. 3,545,971. Suitable synthetic polymers include those described, for example, in U.S. Pat. Nos. 3,142,568 by Nottorf issued July 28, 1964, 3,193,386 by White issued July 6, 1965, 3,062,674 by Houck et al issued Nov. 6, 1962, 3,220,844 by Houck et al issued Nov. 30, 1965, 3,287,289 by Ream et al issued Nov. 22, 1966, 3,411,911 by Dykstra issued Nov. 19, 1968, and 3,488,708 by Smith issued Jan, 6, 1970, and Canadian Pat. No. 774,054 by Dykstra.

The hydrophilic colloid to be hardened is typically utilized as a layer or coating on a support. A wide variety of supports, such as polymeric film, wood, metal, glass and the like, may be utilized to form hydrophilic colloid-coated elements. Where a photographic element is contemplated, the support can take such forms as those set forth in paragraph X of *Product Licensing Index*, Vol. 92, December, 1971, publication 9232, page 108. *Product Licensing Index* is published by Industrial Opportunities Ltd., Homewell, Havant Hampshire, PO9 1EF, United Kingdom.

Where the hydrophilic colloid is to be utilized in combination with a support to form a photographic element, it will contain in or on it a radiation-sensitive material. This material can be panchromatic or orthochromatic material, sensitive only to X-rays or sensitive to selected portions of the electromagnetic spectrum. In one form, the radiation-sensitive portion of the photographic element can contain a single, unitary hydrophilic colloid layer having dispersed therein the radiation-sensitive material, together with photographic addenda to form a photographic emulsion layer or coating. In alternative forms, the radiation-sensitive portion of the photographic element can comprise a plurality of layers with the radiation-sensitive material or materials being contained in some or all of the layers. For example, as is characteristic of color photography, a plurality of layers can be present, sensitized within separate segments of the visible spectrum.

Suitable radiation-sensitive colloid compositions which can be employed in practicing this invention are sensitive to electromagnetic radiation and include such diverse materials as silver salt, zinc oxide, photosensitive polycarbonate resins and the like. Silver halides are preferred radiation-sensitive materials and are preferably associated with a colloid dispersion vehicle to form an emulsion coating or layer. Specific preferred silver halide-containing photographic emulsions and processes for their preparation and use are disclosed in paragraph I of *Product Licensing Index*, Vol. 92, December, 1971, publication 9232, page 107. The radiation-sensitive colloids can additionally include a variety of conventional photographic addenda, such as development modifiers, antifoggants, plasticizers and lubricants, brighteners, spectral-sensitization agents and color-forming materials, as set forth in paragraphs IV, V, XI, XIV, XV and XXII, respectively, of *Product Licensing Index*, Vol. 92, December, 1971, publication 9232, pages 107-110. While it is contemplated that the compounds utilized in the practice of this invention may serve as the sole hardener present, it is appreciated that other conventional hardeners may also be incorporated into the hydrophilic colloid, such as those set forth, for example, in T. H. James, *The Theory of the Photographic Process*, 4th Ed., MacMillan, 1977, pp. 77–87.

While a wide range of concentrations of the bis(vinylsulfonyl)alkane hardeners described herein is effective to harden, a particularly effective concentration is from about 0.5 to about 6 percent by weight, based on the weight of the hardenable material present. This does not include the weight of water present in the colloid. In a preferred range, it has been found that about 1 percent to about 3 percent by weight, based on the weight of hardenable material, is particularly effective in achieving superior hardening. In forming useful hydrophilic colloid-containing aqueous coating compositions from about 10–0.1 percent by weight hydrophilic colloid, based on the weight of water, is conveniently employable, although both higher and lower hydrophilic colloid concentrations can be employed.

The nitro-substituted aromatic compounds are effective as homopolymerization inhibitors in widely varying concentrations. Concentrations as low as $10^{-6}$ mole of inhibitor per mole of bis(vinylsulfonyl)alkane hardener have been found effective. It is preferred for purposes of homopolymerization inhibition to employ concentrations up to about $10^{-2}$ mole of inhibitor per mole of bis(vinylsulfonyl)alkane hardener. However, nitro-substituted aromatic compounds have been employed in photographic elements lacking bis(vinylsulfonyl)alkane hardener for other purposes in substantially higher concentrations. The inhibitors can be employed up to their solubility limits in photographic coating compositions, which is typically less than about 1 mole of inhibitor per mole of bis(vinylsulfonyl)alkane hardener. To avoid any substantial adverse photographic effect, it is preferred that the nitro-substituted aromatic inhibitors be present in a concentration of less than about 0.1 mole per mole of bis(vinylsulfonyl)alkane hardener.

The following examples are included for a further understanding of the invention.

Example 1—Bis(vinylsulfonyl)methane

A. 3,5-Dinitrobenzoic Acid Inhibitor

To a well stirred solution of 53.84 g of bis-(2-chloroethylsulfonyl)methane in 300 ml of acetone containing 0.9 g of 3,5-dinitrobenzoic acid, was added dropwise at 20°–25° C. a solution of 40.48 g of triethylamine in 50 ml of acetone containing 0.15 g of 3,5-dinitrobenzoic acid. The reaction was stirred for 1 hour at 25° C. then cooled to −30° C. and filtered to remove triethylamine hydrochloride. The filtrate was evaporated to dryness on a rotary evaporator at 40° C. and water aspirator pressure. The residue was recrystallized from methanol containing 0.3 percent (wt/vol) of 3,5-dinitrobenzoic acid, to give 29.3 g (75 percent) of colorless crystalline bis(vinylsulfonyl)methane of m.p. 59°–61° C. This material readily dissolved in water to give a 2 percent by weight solution with no insoluble material present.

B. 2,4-Dinitrobenzenesulfonic Acid Sodium Salt Inhibitor

By the procedure used in A, except that sodium 2,4-dinitrobenzenesulfonate was substituted for 3,5-dinitrobenzoic acid, a 16.5 g (85 percent yield) sample (m.p.

59°–61° C.) of bis(vinylsulfonyl)methane was obtained. A 2 percent by weight aqueous solution was made up (no insoluble material) and let stand for more than 10 months at room temperature. Analysis of the still clear solution by high pressure liquid chromatography (HPLC) showed a 1.6 percent concentration of bis(vinylsulfonyl)methane remaining. A sample of the dry compound was also kept at room temperature for more than 10 months. A fresh 2 percent by weight solution made from this sample was found to contain 1.8 percent bis(vinylsulfonyl)methane by HPLC analysis.

C. 2,4-Dinitrobenzoic Acid Inhibitor

By the procedure used in A, except that 2,4-dinitrobenzoic acid was substituted for 3,5-dinitrobenzoic acid, a 15.1 g sample (77 percent yield) of bis(vinylsulfonyl)methane (m.p. 59°–60.5° C.) was obtained. A clear 2 percent by weight aqueous solution containing no insoluble matter was readily made up from this material.

D. Hydroquinone Inhibitor

A 25.6 g sample (65 percent yield) of bis(vinylsulfonyl)methane (m.p. 59°–61° C.) was obtained by the procedure in A except that hydroquinone was substituted for 3,5-dinitrobenzoic acid. This sample of bis(vinylsulfonyl)methane would not dissolve completely in water to form a 2 percent by weight solution: a voluminous flocculent material remained. However, if water containing a minute amount of 3,5-dinitrobenzoic acid was used, a clear 2 percent by weight solution of this bis(vinylsulfonyl)methane was readily formed.

E. No Inhibitor

Using the procedure of A with no inhibitor and very pure bis(2-chloroethylsulfonyl)methane a 7.0 g sample (36 percent yield) of bis(vinylsulfonyl)methane (m.p. 59°–61° C.) was obtained after recrystallization from ethyl acetate.

Uninhibited bis(vinylsulfonyl)methane is only slightly soluble in distilled water and only partially soluble in distilled water containing hydroquinone because of rapid polymerization. However, the uninhibited vinyl compound readily forms clear and stable 2 percent by weight solutions in distilled water containing 3,5-dinitrobenzoic acid.

Effective Levels of Inhibitor in Solution

Samples of uninhibited bis(vinylsulfonyl)methane (BVSM) were completely dissolved in distilled water containing various levels of 3,5-dinitrobenzoic acid (3,5-DNBA) to form 2 percent by weight solutions with the following molar ratios of inhibitor to vinyl compound:

$1.8 \times 10^{-6}$ mole 3,5-DNBA/mole BVSM,
$4.6 \times 10^{-6}$ mole 3,5-DNBA/mole BVSM,
$9.2 \times 10^{-6}$ mole 3,5-DNBA/mole BVSM,
$1.8 \times 10^{-5}$ mole 3,5-DNBA/mole BVSM, and
$2.8 \times 10^{-5}$ mole 3,5-DNBA/mole BVSM.

These solutions were held at room temperature for 22 days and were periodically analyzed for vinylsulfone content. During this time, no solution showed any decrease in vinylsulfone concentration within experimental error.

The invention has been described with particular reference to preferred embodiments thereof, but it will be understood that variations and modifications can be effected within the spirit and scope of the invention.

We claim:

1. A photographic hardener composition consisting essentially of a bis(vinylsulfonyl)alkane hardener and a nitro-substituted aromatic compound in an amount sufficient to inhibit homopolymerization of the hardener, said nitro-substituted aromatic compound is of the formula:

where
Ar is an aromatic hydrocarbon of from 6 to 12 carbon atoms.
Ball is a polar group and
n and m are independently chosen from among the integers 1, 2 and 3, provided that when Ar is a benzene moiety m is at least 2 and the sum of m+n is 5 or less.

2. A photographic hardener composition according to claim 1 wherein the hardener is of the formula:

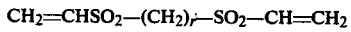

where
r is selected from among the integers 1, 2 and 3.

3. A photographic hardener composition consisting essentially of a bis(vinylsulfonly)alkane hardener and a nitro-substituted aromatic compound in an amount sufficient to inhibit homopolymerization of the hardener, said nitro-substituted aromatic compound is of the formula:

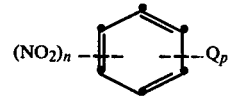

where
Q is COZ or SO$_2$Z;
Z is —OM, —OR or —NR$_2$;
R is hydrogen or alkyl of from 1 to 6 carbon atoms,
M is a salt-forming cationic moiety,
n is an integer of the value 1, 2 or 3; and
p is an integer of the value 1 or 2, the sum of n+p being 4 or less.

4. A photographic hardener composition accordto claim 1 wherein the nitro-substituted aromatic compound is present in a concentration of from $10^{-6}$ to 0.1 mole per mole of hardener.

5. A photographic hardener composition consisting essentially of bis(vinylsulfonyl)methane and from $10^{-6}$ to $10^{-2}$ mole of a dinitrobenzoic acid per mole of bis(vinylsulfonyl)methane.

6. An aqueous coating composition useful in forming a layer of a photographic element comprising a hydrophilic colloid at least partially forehardened with a bis(vinylsulfonyl)alkane hardener and, in an amount sufficient to inhibit homopolymerization of the hardener, a nitro-substituted aromatic compound of the formula:

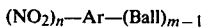

where
Ar is an aromatic hydrocarbon of from 6 to 12 carbon atoms;
Ball is a polar group; and n and m are independently chosen from among integers of the value 1, 2 and 3, provided that when Ar is a benzene moiety m is at least 2 and the sum of m+n is 5 or less.

7. An aqueous coating composition according to claim 6 wherein the hardener is of the formula:

where
r is selected from among the integers 1, 2 and 3.

8. An aqueous coating composition according to claim 6 wherein the nitro-substituted aromatic compound is of the formula:

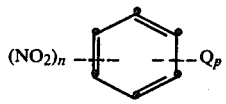

where
Q is COZ or $SO_2Z$;
Z is —OM, —OR or —$NR_2$;
R is hydrogen or alkyl of from 1 to 6 carbon atoms,
M is a salt-forming cationic moiety,
n is an integer of the value 1, 2 or 3; and
p is an integer of the value 1 or 2, the sum of n+p being 4 or less.

9. An aqueous coating composition useful in forming a layer of a photographic element comprised of gelatin hardened with from 0.5 to 6 percent by weight bis(vinylsulfonyl)methane, based on the dry weight of the gelatin prior to hardening, and from $10^{-6}$ to $10^{-2}$ mole dinitrobenzoic acid per mole of bis(vinylsulfonyl)methane introduced in forming the composition.

10. In a process of hardening an aqueous coating composition useful in forming a layer of a photographic element comprising adding a bis(vinylsulfonyl)alkane hardener to a hydrophilic colloid, the improvement comprising inhibiting homopolymerization of the hardener with a nitro-substituted compound of the formula:

where
Ar is an aromatic hydrocarbon of from 6 to 12 carbon atoms;
Ball is a polar group; and
n and m are independently chosen from among integers of the value 1, 2 and 3, provided that when Ar is a benzene moiety m is at least 2 and the sum of m+n is 5 or less.

11. In a process of preparing a photographic element by adding a bis(vinylsulfonyl)alkane hardener to a coating composition containing a hydrophilic colloid and coating the composition onto a photographic support, the improvement comprising inhibiting homopolymerization of the hardener with a nitro-substituted aromatic compound of the formula:

where
Ar is an aromatic hydrocarbon of from 6 to 12 carbon atoms;
Ball is a polar group; and
n and m are independently chosen from among integers of the value 1, 2 and 3, provided that when Ar is a benzene moiety m is at least 2 and the sum of m+n is 5 or less.

12. In a process according to claim 11 wherein the hardener is of the formula:

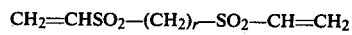

where
r is selected from among the integers 1, 2 and 3.

13. In a process according to claim 11 wherein the nitro-substituted aromatic compound is of the formula:

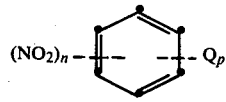

where
Q is COZ or $SO_2Z$;
Z is —OM, —OR or —$NR_2$;
R is hydrogen or alkyl of from 1 to 6 carbon atoms,
M is a salt-forming cationic moiety,
n is an integer of the value 1, 2 or 3; and
p is an integer of the value 1 or 2, the sum of n+p being 4 or less.

14. In a process according to claim 11 wherein the nitro-substituted aromatic compound is added in a concentration of from $10^{-6}$ to 0.1 mole per mole of hardener.

15. In a process of preparing a photographic element by adding to a gelatin-containing coating composition from 0.5 to 6 percent by weight, based on the weight of the gelatin, of bis(vinylsulfonyl)methane, the improvement comprising inhibiting homopolymerization of the bis(vinylsulfonyl)methane with from $10^{-6}$ to $10^{-2}$ mole per mole of bis(vinylsulfonyl)methane of a dinitrobenzoic acid.

16. In a photographic element comprising a support and, coated on the support, one or more layers, at least one of which is radiation-sensitive, containing a hydrophilic colloid at least partially forehardened with a bis(vinylsulfonyl)alkane hardener, the improvement wherein the layer or layers contains, in an amount sufficient to inhibit homopolymerization of the hardener, a nitro-substituted aromatic compound of the formula:

where
Ar is an aromatic hydrocarbon of from 6 to 12 carbon atoms;
Ball is a polar group; and
n and m are independently chosen from among integers of the value 1, 2 and 3, provided that when Ar is a benzene moiety m is at least 2 and the sum of m+n is 5 or less.

17. In the improved photographic element according to claim 16 wherein the hardener is of the formula:

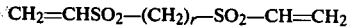

where
r is selected from among the integers 1, 2 and 3.

18. In the improved photographic element according to claim 16 wherein the nitro-substituted aromatic compound is of the formula:

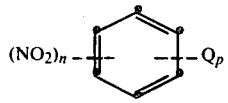

where
Q is COZ or SO$_2$Z;
Z is —OM, —OR or —NR$_2$;
R is hydrogen or alkyl of from 1 to 6 carbon atoms,
M is a salt-forming cationic moiety,
n is an integer of the value 1, 2 or 3; and
p is an integer of the value 1 or 2, the sum of n+p being 4 or less.

19. In a photographic element comprised of a support and, coated on the support, one or more gelatino-silver halide emulsion layers forehardened with a bis(vinylsulfonyl)methane, the improvement comprising a homopolymerization inhibiting amount of one or a combination of dinitrobenzoic or dinitrobenzenesulfonic acid, or the methyl, ethyl or propyl esters or alkali metal salts thereof.